United States Patent
Neilan et al.

(10) Patent No.: US 10,247,661 B2
(45) Date of Patent: Apr. 2, 2019

(54) OPTICAL TECHNIQUE FOR COATING CHARACTERIZATION

(71) Applicant: Cook Medical Technologies LLC, Bloomington, IN (US)

(72) Inventors: John Neilan, Gort (IE); Syed A. M. Tofail, Castletroy (IE); Rabah Mouras, Annacotty (IE); Christophe Silien, Co. Limerick (IE); Aladin Mani, Co. Limerick (IE); David Murray, Co. Limerick (IE)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 73 days.

(21) Appl. No.: 15/652,583

(22) Filed: Jul. 18, 2017

(65) Prior Publication Data
US 2018/0024048 A1    Jan. 25, 2018

Related U.S. Application Data

(60) Provisional application No. 62/364,380, filed on Jul. 20, 2016.

(51) Int. Cl.
*G01N 21/21* (2006.01)
*A61L 31/08* (2006.01)
(Continued)

(52) U.S. Cl.
CPC ............ *G01N 21/21* (2013.01); *A61L 29/16* (2013.01); *A61L 31/08* (2013.01); *A61L 31/16* (2013.01);
(Continued)

(58) Field of Classification Search
CPC ....................................................... G01N 21/21
(Continued)

(56) References Cited

U.S. PATENT DOCUMENTS 4,853,252 A * 8/1989 Frankel ................... B41M 5/398
427/596
5,616,373 A * 4/1997 Karner ................... C23C 16/272
427/122
(Continued)

FOREIGN PATENT DOCUMENTS

WO  WO 2006/114705     11/2006
WO  WO 2007/106441 A2   9/2007
(Continued)

OTHER PUBLICATIONS

Munhoz, F. et al., "Polarization-Resolved Four-Wave Mixing Microscopy for Structural Imaging in Thick Tissues", *Journal of the Optical Society of America*, vol. 29, No. 6, Jun. 1, 2012, pp. 1541-1550.
(Continued)

*Primary Examiner* — Tarifur R Chowdhury
*Assistant Examiner* — Omar H Nixon
(74) *Attorney, Agent, or Firm* — Brinks Gilson & Lione (57) ABSTRACT

The present invention generally relates to methods for determining the presence and distribution of a polarization active material present in a coating. In one embodiment, the coating is present on an implantable device, for example an implantable stent.

18 Claims, 8 Drawing Sheets

(51) Int. Cl.
*A61L 31/16* (2006.01)
*A61L 29/16* (2006.01)
*G01B 9/04* (2006.01)
*G01B 11/06* (2006.01)
*G02B 21/00* (2006.01)

(52) U.S. Cl.
CPC ............ *G01B 9/04* (2013.01); *G01B 11/0641* (2013.01); *G02B 21/0092* (2013.01); *A61L 2300/416* (2013.01); *A61L 2300/606* (2013.01)

(58) Field of Classification Search
USPC .......................................................... 356/364
See application file for complete search history.

(56) References Cited

U.S. PATENT DOCUMENTS

| | | | |
|---|---|---|---|
| 6,046,448 A * | 4/2000 | Sato | G01N 21/21 250/225 |
| 6,306,489 B1 * | 10/2001 | Hellmann | B24C 1/06 428/142 |
| 7,108,970 B2 | 9/2006 | Levinson | |
| 7,420,675 B2 | 9/2008 | Giakos | |
| 7,462,237 B2 | 12/2008 | Specht et al. | |
| 7,564,541 B2 | 7/2009 | Tuschel | |
| 8,126,205 B2 | 2/2012 | Levenson et al. | |
| 8,488,120 B2 | 7/2013 | Hall et al. | |
| 8,669,360 B2 | 3/2014 | Zeng et al. | |
| 8,730,468 B2 | 5/2014 | Messerchmidt | |
| 8,951,595 B2 | 2/2015 | Stankus et al. | |
| 8,961,727 B2 | 2/2015 | Jackson et al. | |
| 9,063,072 B1 | 6/2015 | Lee | |
| 2004/0129867 A1 | 7/2004 | Mackey | |
| 2005/0264813 A1 * | 12/2005 | Giakos | B82Y 20/00 356/369 |
| 2006/0021563 A1 * | 2/2006 | Nollert-von Specht | C30B 7/00 117/68 |
| 2006/0170808 A1 | 8/2006 | Biernath et al. | |
| 2007/0212394 A1 * | 9/2007 | Reyes | A61F 2/91 424/423 |
| 2008/0020013 A1 * | 1/2008 | Reyes | A61F 2/91 424/423 |
| 2008/0194928 A1 | 8/2008 | Bandic et al. | |
| 2011/0189601 A1 * | 8/2011 | Koshiba | G03F 7/20 430/30 |
| 2011/0257732 A1 | 10/2011 | McLain et al. | |
| 2011/0264190 A1 | 10/2011 | McClain et al. | |
| 2013/0302381 A1 | 11/2013 | Barnett | |
| 2015/0050428 A1 * | 2/2015 | Baillin | C23C 18/02 427/550 |

FOREIGN PATENT DOCUMENTS

| | | |
|---|---|---|
| WO | WO 2013/144891 A2 | 10/2013 |
| WO | WO 2014/060118 | 4/2014 |

OTHER PUBLICATIONS

Ribeiro, J.F. et al., "Skin Collagen Fiber Molecular Order: A Pattern of Distributional Fiber Orientation as Assessed by Optical Anisotropy and Image Anaylsis", *PLoS One*, vol. 8, No. 1, Jan. 18, 2013, 9 pages.

Extended European Search Report in corresponding European Application No. 17182114.3, dated Nov. 3, 2017, 6 pages.

Dieng, T. et al., "Confocal Raman Microsopy", *Springer Series in Optical Sciences*, 2011, 306 pages.

Buntz, B., "Bringing a Sharper Focus to Quality Control of Coated Surfaces", *European Medical Device Technology*, Oct. 29, 2010, 6 pages, and Retrieved from the Internet on Nov. 16, 2015 at http://www/emdt.co.uk/article/bringing-sharper-focus-quality-controls-surfaces.

* cited by examiner

OPTICAL TECHNIQUE FOR COATING CHARACTERIZATION

RELATED APPLICATIONS

This non-provisional patent application claims priority to U.S. Provisional Patent Application No. 62/364,380, filed Jul. 20, 2016, the contents of which are incorporated by reference in their entirety.

TECHNICAL FIELD

The present invention generally relates to methods for determining the presence and distribution of a polarization active material in a coating. In one embodiment, the coating is present on an implantable device, for example, an implantable stent. In another embodiment, the polarization active material is a crystalline drug.

BACKGROUND

Local delivery of a therapeutic agent can be useful in the treatment of many medical conditions. Illustratively, local delivery of a therapeutic agent within a body vessel or to a selected portion of internal body tissue can eliminate or reduce the need for systemic delivery of the therapeutic agent, thus minimizing any potential adverse effect of the therapeutic agent on areas of the body not needing treatment.

Minimally invasive implantable medical devices, such as balloons, catheters and stents, can provide a platform for delivering therapeutic agents to internal body tissue. For example, balloon catheters or stents may be used to deliver a therapeutic agent directly to the target site within a body vessel, such as an artery or vein.

One example of a condition that can be beneficially treated by local administration of a therapeutic agent with a balloon catheter is the delivery of a therapeutic agent in combination with percutaneous transluminal coronary angioplasty (PTCA), a technique used to dilate stenotic portions of blood vessels. Although PTCA and related procedures aid in alleviating intraluminal constrictions, such constrictions or blockages may reoccur in many cases. The cause of these recurring obstructions, termed restenosis, may be due to the body responding to the surgical procedure. Restenosis of the vessel may develop over several months after the procedure, and may require another angioplasty procedure or a surgical bypass operation to correct. Proliferation and migration of smooth muscle cells (SMC) from the media layer of the lumen to the intimal layer may cause an excessive production of extracellular matrices (ECM), which is believed to be one of the leading contributors to the development of restenosis. The extensive thickening of tissues narrows the lumen of the blood vessel, constricting or blocking the blood flow through the vessel.

Drugs that inhibit restenosis may be locally delivered during PTCA from a catheter or by placement of a stent configured to continue to release the drug after the PTCA procedure. The delivery of the drug from coatings in these and other minimally invasive procedures can be complicated by the need to have a coating that is durable during delivery, but which effectively delivers the drug when implanted in the region where local treatment is desired. Because natural biological environments are aqueous, it can occur that a coating containing a water-insoluble drug is sufficiently durable during travel to the intended delivery site, but then fails to optimally deliver the drug at the site. Needs thus exist for compositions, coatings, and coated implantable medical devices which enable the beneficial delivery of a drug locally to a site intended for treatment.

The complexity of the issues associated with drug-coated products, such as drug coated stents, arises due to the inherent hybrid nature of the product. Such products consists of a drug, which is typically a soft matter and a delivery device, such as a stent, which is typically made of a hard material such as a plastic, metal or a metal alloy. Typically, the drug coating is applied directly onto the surface of the stent and the drug is held through weak Van der Waals forces. All these factors contribute to the key problem: the control and monitoring of drug coating uniformity during the production process to ensure the right dosage of drug and the proper coverage of drug on the required surface of the device. When the drug is capable of taking multiple polymorphic forms additional problems may arise that require characterization of the amounts of individual polymorphic forms present in the coating.

BRIEF SUMMARY

One aspect of the present invention provides a method for determining a distribution of a polarization active compound in a coating. In one embodiment, the method includes utilizing optical microscopy, such as confocal microscopy, to obtain images at a number of planes at differing axial positions between the upper and lower boundaries of the coating. The distribution of polarization activity is measured within each of the images. A three-dimensional distribution of the polarization active material is constructed based on the distribution of polarization activity within each of images and the distribution of the polarization active compound in the coating determined based on the three dimensional distribution.

The non-polarization active compound may be a crystalline taxane polymorph, for example, a crystalline paclitaxel polymorph. The coating may be a coating on an implantable device, for example, an implantable stent or balloon. In some embodiments, the coating consists essentially of the polarization active compound, for example, a drug. In other embodiments, the coating is free of a polymeric or non-polymeric carrier material.

In yet other embodiments, the method also includes determining the distribution of a second non-polarization active compound in the coating based on the three-dimensional polarization activity distribution. Here, the first and second polarization active compounds are compounds that exhibit different polarization activity properties. The first and second compounds can be crystalline polymorphs of paclitaxel. For example, the first polarization active compound can be di-hydrate paclitaxel and the second polarization active compound can be anhydrous paclitaxel.

The method may also include determining the thickness of the coating including determining the axial position of a first and a second focal plane and determining a thickness of the coating based the axial position of these focal planes. The first focal plane may be positioned at an upper boundary of the coating and the second focal plane at a lower boundary of the coating.

In certain embodiments the confocal optical microscopy includes illuminating the coating with laser light at a wavelength of 786 nm, 380 nm or 229 nm.

BRIEF DESCRIPTION OF THE DRAWINGS

FIGS. 1(A-B) are illustrations of a modelled optical scattering response of paclitaxel with polarization activity illuminated with X-polarized light (FIG. 1(A)) and Z-polarized light (FIG. 1(B)).

FIGS. 2(A-B) are schematics of the geometry of polarization microscope modelling in COMSOL (FIG. 2(A)) and wire-grid polarizer geometry and pitch (FIG. 2(B)).

FIG. 3(A-C) is an illustration of plane polarized light transmission from wire-grid polarizer with X-polarization (FIG. 3(A)) and Z-polarization (FIG. 3(B)) and illustration of laser beam splitup at beam-splitter (FIG. 3(C)).

FIG. 4(A-B) illustrates the Geometry of paclitaxel step and needles-like structure used in simulation (FIG. 4(A)) and light view of a complete polarization microscope with paclitaxel needles (FIG. 4(B)).

FIG. 5(A-B) are graphs showing modelled scattered intensity calculated at the detector at a step profile using non-polarization active values of 0.01 (FIG. 5(A)) and 0.001 (FIG. 5(B)).

FIG. 6(A-C) are graphs showing modelled scattered intensity calculated at the detector of paclitaxel needle-like structures using 380 nm and non-polarization active values of 0.01 (FIG. 6(A)) and 0.001 (FIG. 6(B)).

DETAILED DESCRIPTION

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Each disclosed feature or features can be combined with the generalized features discussed herein, to form a disclosed embodiment of the present invention.

Characterization of Coatings

One aspect of the present invention provides a method for the detection and determination of the amount of a compound present in a coating on a device. In some cases, the device is a device sized and shaped for at least partial implantation into the body of a human or veterinary patient. For example, the device may be a stent, catheter, balloon, wire guide or cannula. However, the present method is applicable for the characterization of coatings in general.

One embodiment of the method utilizes a combination of polarized optical microscopy and confocal microscopy to characterize the composition and thickness of a coating on a surface of the device, for example, the implantable device. In another embodiment, the method utilizes birefringent microscopy in combination with confocal microscopy to characterize the amount and/or distribution of one or more compounds exhibiting polarization activity properties.

Confocal microscopy is a technique that uses pinholes placed between the detector and the sample in a microscope stage to select the information from a single focal plane and to reject unwanted signals from regions outside that focal plane. The technique allows for the production of a sharply focused optical slice through the sample. This allows both high contrast depth and surface imaging. Generating a series of two-dimensional (2D) images at different depth levels in the sample, for example a coating, creates a three-dimensional (3D) data set. The 3D imaging capability of confocal microscopy offers an alternative approach to conventional optical microscopy to measurement of coating thickness with high resolution.

Moreover, if the coating is anisotropic, the polarization activity properties of the coating can be exploited with the polarization microscopic scheme to investigate the structure and morphology of the coating. The confocal setup can be used to measure the thicknesses below 10 microns. Adding a Nomarski prism that splits a laser beam into two beams with orthogonal polarizations (s and p) allows simultaneous measurement of thickness and refractive index of the coating. This method, termed dual-beam confocal microscopy, is based on the creation of two closely spaced lateral confocal gates for the two orthogonal polarization states of a laser beam in a sample via a Nomarski prism.

In certain embodiments, the coating is illuminated by a focused laser beam having a wavelength of between 20 microns and 100 nm, or between 10 microns and 100 nm, or between 1 micron and 100 nm. The wavelength used is chosen depending on the composition and thickness of the coating. Preferred wavelengths include 786 nm, 380 nm and 229 nm. Generally, a shorter wavelength will provide a more precise measure of the structure and thickness of the coating. Preferably, the wavelength is less than half of the typical thickness of the coating. For coating having a thickness in the range 10-20 microns, the wavelength used should typically less than 10 microns.

Polarization active materials include birefringent materials, dichroic materials, and optically active materials. Optical activity (sometimes referred to as rotary polarization) is the rotation of the plane of polarization of linearly polarized light as it travels through certain materials. Birefringence (also called double refraction) is characterized by the dependence of the speed of monochromatic light on polarization. Circular birefringence (CB) occurs when the speeds of left and right circular polarized light differ and linear birefringence (LB) occurs when the speeds of two orthogonal linearly polarized light beams differ. CB is the most common phenomenon and gives rise to a rotation of the polarization plane of linearly polarized light. When these phenomena are caused under the influence of an applied magnetic field they are termed magnetic circular birefringence (MCB) and magnetic linear birefringence (MLB). Dichroism is the dependence of the absorption (or emission) of monochromatic light on polarization. Circular dichroism (CD) occurs when the absorptions (or emissions) of left and right circularly polarized light in matter differ and linear dichroism (LD) when the absorptions (emissions) of two orthogonal linearly polarized light beams differ. In the case that these phenomena are caused under the influence of an applied magnetic field they are called magnetic circular dichroism (MCD) and magnetic linear dichroism (MLD.)

Where two or more polarization active materials having differing properties, e.g. materials that rotate the polarization of light by different amounts, are present in the coating, birefringence polarization microscopy may be used to characterize the amount of each of the materials present in the coating.

Chiral molecules, including biological samples and pharmaceutical drugs, are inherently polarization active. In addition, crystals with asymmetric crystal structures often exhibit polarization activity, as are plastics under mechanical stress.

The method disclosed herein provides for the determination of the amount and distribution of a polarization active compound in a coating. In a preferred embodiment, the compound is a drug, for example a crystalline drug exhibiting birefringence. Examples of such drugs include taxanes, mTOR inhibitors, such as rapamycin, and solid dose pharmaceuticals.

Polymorphism is the ability of a solid material to exist in more than one form or crystal structure. Many drugs exist in different polymorphic forms. For example, taxane analogues and derivatives, such as paclitaxel, exist as multiple polymorphs. Taxane compounds are often used as therapeutic agents coated on and released from implantable devices, such as stents, to mitigate or prevent restenosis. Paclitaxel is believed to disrupt mitosis (M-phase) by binding to tubulin to form abnormal mitotic spindles (i.e., a microtubule stabilizing agent). A therapeutic compound such as paclitaxel can crystallize as more than one distinct crystalline species (i.e., having a different arrangement of molecules in a solid form) or shift from one crystalline species to another. Polymorphs can exhibit different optical properties, melting points, solubilities, chemical reactivities, dissolution rates, and different bioavailabilities. Of particular relevance here is the observation that different polymorphs sometimes exhibit different polarization activity.

Solid forms of paclitaxel at room temperature include amorphous paclitaxel, dihydrate crystalline paclitaxel and anhydrous crystalline paclitaxel. The amorphous polymorph of paclitaxel is not polarization active. However, both the dihydrate and anhydrous polymorphs exhibit polarization activity. The different polarization properties of the crystalline paclitaxel polymorphs provide a means of characterizing the amount and distribution of these polymorphs in a coating.

In one embodiment of the method, the thickness of a coating is determined by measuring the higher scattering that occurs due to the Fresnel reflection at the interfaces exhibiting step variation of the refractive index. This method may be utilized to measure the thickness of a coating including non-birefringent, as well as birefringent, materials. For example, the thickness of a coating containing only amorphous paclitaxel may be determined by this method using an axial scanning confocal microscope to obtain a series of optical slices from different known focus levels in the coating. Increased scattering occurs at the air/coating interface because of the differing refractive indices of the air and the coating material. Similarly, increased scattering occurs at the interface between the bottom of the coating layer and the base material of the device. For example, if the device is a drug coated metallic stent, increased scattering will occur at the interface between the bottom of the drug coating and the metallic surface, for example, a stainless steel or nickel-titanium alloy surface.

If a polarization active material is present in the coating, the presence of this material may be determined by characterizing the polarization activity from the material. In one embodiment, images are obtained from the material in a number of optical planes at differing levels in the coating and a three-dimensional image of the coating constructed from a combination of the images. This allows for the amount and distribution of the material to be determined. Where two of more polarization active compounds having different optical properties are present in the coating, for example, dihydrate and anhydrous paclitaxel, the amount and distribution of each of the compounds may be determined using this method.

The method may be utilized to determine the distribution of paclitaxel, or another polarization active compound, in a coating including only that compound. For example, where the coating includes only paclitaxel, the amount and distribution of the paclitaxel may be determined. Where more than one polymorph of paclitaxel is present in the coating, the amount and distribution of each polymorph may be determined.

When the coating includes carrier materials, excipients or other additional materials, the amount and distribution of the drug may be determined so long as the drug can be distinguished from the other materials on the basis of its polarization activity For example, the distribution of a polarization active compound, for example paclitaxel, may be determined in a coating also including a carrier material that delays the release of the paclitaxel, or other material, from the device after implantation. Here, the paclitaxel may be mixed with the carrier material. Examples of such carrier materials include, but are not limited to, biostable and bioabsorbable polymeric materials.

In yet other embodiments, the coating may include an excipient, such as urea and/or urea derivatives, gallates and gallate derivatives (such as epi gallo catechin gallate), tannic acid, saccharides and/or saccharide derivatives, chitin and/or chitin derivatives, ascorbic acid, citric acid, sterates and/or sterate derivatives, polyvinyl pyrolidone, dicalcium phosphate dihydrate, eudragit polymers and/or eudragit polymers derivatives, cellulose and/or cellulose derivatives, PEG, polysorbate 80, sodium lauryl sulphate, chitosan, magnesium dioxide, silicon dioxide, carbonate derivatives, plasdone, butylated hydroxyanisole, succinic acid, sodium dioctyl sulfosuccinate, precirol ATO 5, or combinations of a least two of these excipients. The excipient is a compound that speeds up the release of the drug when the device is deployed within the patient, for instance by the excipient dissolving within the patient's blood plasma and providing for quick release of the drug. The presence of an excipient offers particular advantages when used in coatings of drug coated balloons that are typically implanted within the body for short periods.

In other embodiments, a combination of one or more layers of drug, mixtures of carrier material/drug, and/or excipient/drug are present on the surface of the device. The layer including the dug may also be over-coated with one or more barrier layers to delay the release of the drug.

Implantable Medical Devices

By way of example, the medical device can be or include a catheter, a wire guide, a stent, a coil, a needle, a graft, a filter, a balloon, a cutting balloon, a scoring balloon, a weeping (perfusion) balloon, or any combination of these. Suitable stents include those without a covering, for example the Cook ZILVER®—PTX stent available from Cook Medical. Suitable stents also include those with a sheath covering. Suitable coils include embolization coils. Suitable wire guides include for instance traditional wire guides as well as wire guides with an attached expandable structure for expansion within a blood vessel lumen, such as a coil, where the expandable structure can optionally carry the coating or coatings as disclosed herein. These or other implants, in certain preferred embodiments, have at least a portion that is configured to expand during deployment so as to contact walls of the passage in which they are implanted to anchor within the passage. In this regard, both self-expanding and force-expandable (e.g. balloon-expandable) stents or other implantable medical devices are contemplated as being within the scope of embodiments of the present invention.

The coating can be a coating on an implantable medical device made from any suitable material or combination of materials. Illustratively, the implantable medical device can include a metal such as stainless steel, tantalum, titanium, nitinol, cobalt, chromium, nickel, molybdenum, manganese, gold, platinum, inconel, iridium, silver, tungsten, elgiloy, alloys of any of these, or another biocompatible metal; carbon or carbon fiber; a calcium-containing inorganic material such as a ceramic; a material composed of ceramic and metallic components (cermet); or a polymeric material. The material of construction for the implantable medical device structure can be biodegradable or nonbiodegradable. Non-biodegradable polymers that can be used include, for example, cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures of these. Biodegradable polymers that can be used include, for example, polylactic acid (PLA), polyglycolic acid (PGA), poly(lactic-co-glycolic acid) (PLGA), polyanhydride, polycaprolactone, polyhydroxybutyrate valerate, or mixtures of these. Biodegradable metals may also be used, including for example a biodegradable magnesium alloy.

In some preferred embodiments herein, the implantable medical device is or includes a stent, such as a vascular stent. Such a stent may for example be a force-expandable stent, such as a balloon-expandable stent, or a self-expanding stent. The stent may be made from any one of numerous metals and alloys, including those identified herein. The structure of the stent may be formed in a variety of ways to provide a suitable intraluminal support structure having an outer surface for contact with the vessel wall upon implantation and an inner surface that faces the lumen of the vessel and that can be generally opposite the outer surface. For example, the stent may be made from a woven wire structure, a laser-cut cannula, individual interconnected rings, or another pattern or design. In these or other constructions, the stent can include a plurality of struts each having an outer surface for contact with the vessel wall and an inner surface for facing the lumen of the vessel.

Such stents may be force-expandable, such as balloon-expandable, or self-expanding, as discussed above. Self-expanding stents of this type can be made of a resilient metal, preferably a superelastic metal alloy such as a superelastic nickel-titanium (Ni—Ti) alloy, as occurs for example in the ZILVER® PTX stent commercially available from Cook Medical.

In other preferred embodiments, the implantable medical device is or includes a balloon catheter, such as an angioplasty balloon catheter, a weeping or infusion balloon, a scoring balloon catheter or a cutting balloon catheter. Such a balloon catheter can include at least one balloon mounted on a catheter shaft, with the catheter shaft defining an inflation lumen fluidly communicating with an interior of the balloon. The catheter shaft can also define a guide member lumen, for receiving an elongate guidewire or other guiding member for the catheter. The guide member lumen can extend from a distal opening distal to the balloon to a proximal opening proximal to the balloon.

The balloon(s) of the balloon catheters herein may be configured for vascular angioplasty, and/or may have a balloon wall made of any suitable balloon wall material, typically a polymeric balloon wall material. The polymeric or other balloon wall material can be elastomeric, as in the case of an illustrative silicone elastomer, latex rubber elastomer, nylon elastomer, or polyurethane elastomer balloon film, where the balloon can expand upon inflation due to the expansion and thinning of the balloon wall material. Preferred balloon wall materials for non-compliant or semi-compliant balloons include polyamide (e.g. as in Nylon balloons), polyethylene terephthalate (PET), or polyurethane polymers.

Example 1—Element Method COMSOL Wave-Optics Module Studies

The theoretical study was performed on the 2-dimensional system using finite element method COMSOL, wave-optics module (COMSOL, Inc. Burlington, Mass. 01803 USA.)

Figure 1A:
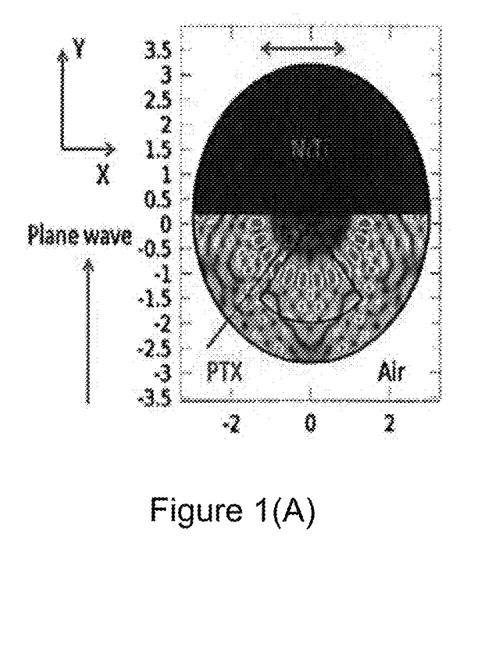
Figure 1B:
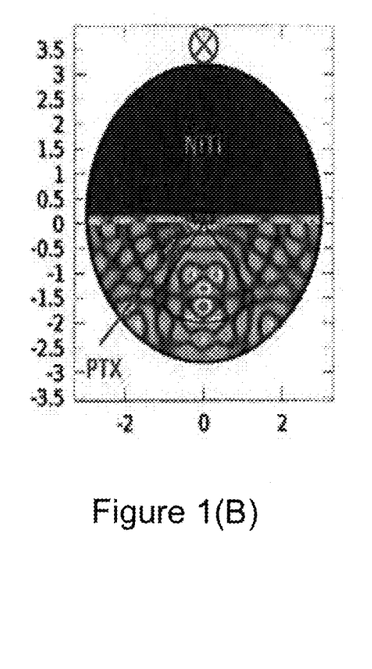

Initially, a small paclitaxel film with specified polarization activity was modelled as shown in FIG. 1. Here, the optical response of the paclitaxel film is sensitive to the polarization of the laser beam whether it is parallel (p-pol) or perpendicular (s-pol) to the plane of incidence. These differences for s and p polarizations indicate that that the polarization activity can be exploited to measure the thickness of the film.

Figure 2A:
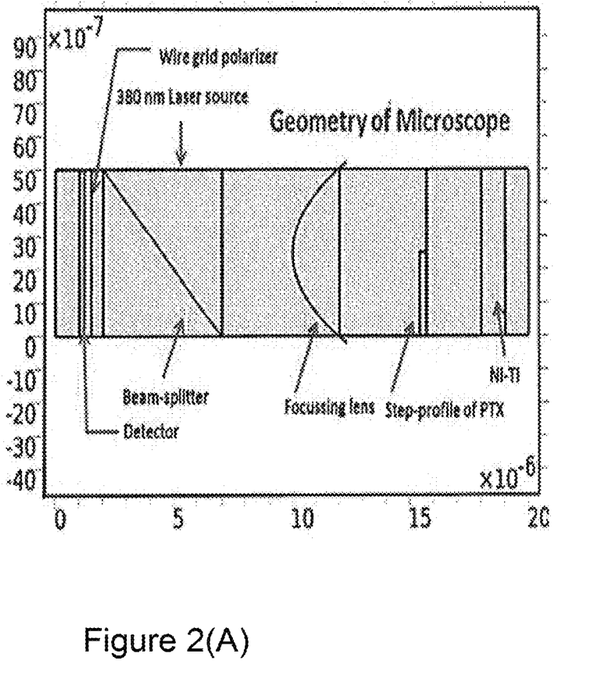
Figure 2B:
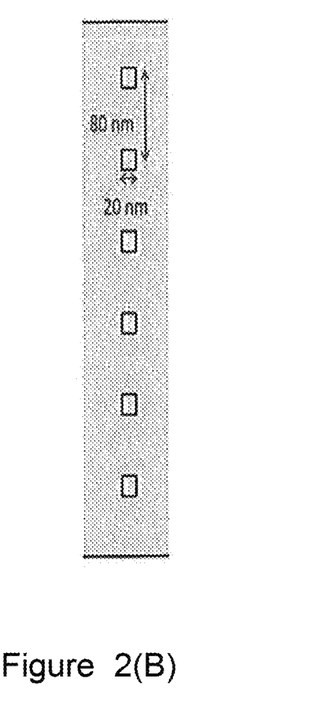

Since COMSOL requires high computational resources for modelling real time optical components, the complete polarization based microscope was modelled in the physical dimension of order of microns with largely reduced sizes of all optical components. All components used to simulate the microscope are illustrated in FIG. 2(A-B) and details are given in table 1.

TABLE 1

| Optical components used in model | |
|---|---|
| Component type | Details |
| Light source and wavelength | Gaussian beam (Laser) at 785 nm, 380 nm and 229 nm |
| Beam-splitter | Glass |
| Aspheric lens | Employs as objective and glass material |
| Step profile | Step profile with refractive index 1.64 |
| Base material | Ni—Ti |
| Refractive index of Ni—Ti alloy | 5.505 + i * 29.045 |
| Detector | A plane surface to calculate scattered intensity from PTX |
| Wire-grid polariser (WGP) | Made of aluminium |
| Refractive index of aluminium | 1.26 + i * 7.27 |

Laser beam emitting from port is split into transmitted and reflected beam by a beam-splitter. The light source size is 5 um. The transmitted beam is absorbed by the scattering boundary and reflected beam is directed towards the focusing lens (Objective). This lens is aspherical plano-convex element that focuses light without any aberrations in order to achieve aberration-free resolution. Light focused on the paclitaxel step is back-scattered and collected by the same lens and again split into the transmitted and reflected beams by the beam-splitter. The reflected beam is again absorbed by the scattering boundary and the transmitted beam is passed through the analyzer to the detector, where the light intensity is calculated.

When s-polarized light is incident on paclitaxel film, it is divided into ordinary (o-ray) and extraordinary ray (e-ray). Both rays propagate with different velocities due to the birefringence of the paclitaxel, are reflected back at paclitaxel-NiTi interface, leave the paclitaxel film and combine together, respectively. The polarization plane of reflected beam is rotated by an amount proportional to the birefringence of the paclitaxel film. The light beam with a rotated plane of polarization passes through the analyzer and the transmitted intensity is a measure of the thickness of the film.

Figure 3A:
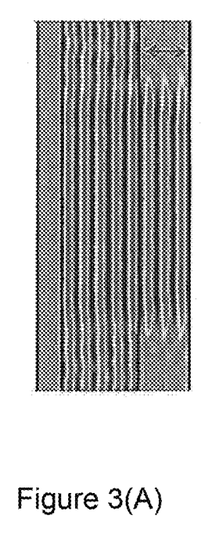
Figure 3B:
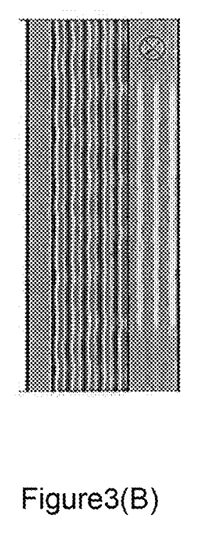
Figure 3C:
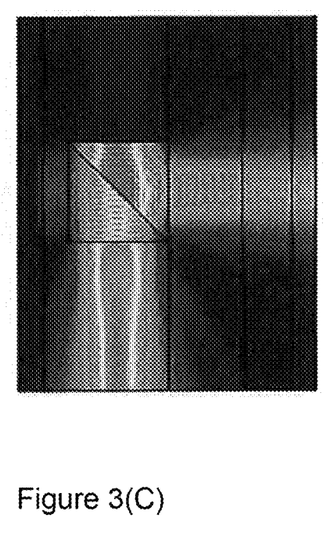

As an example, a wire-grid polarizer ("WGP") performance is investigated with varying pitch and dimensions of the wires and optimized the design for high extinction ratio. FIG. 3 shows performance of WGP and we achieved extinction ratio of 25.

Example 2—Paclitaxel Birefringence Response Study

Figure 4A:
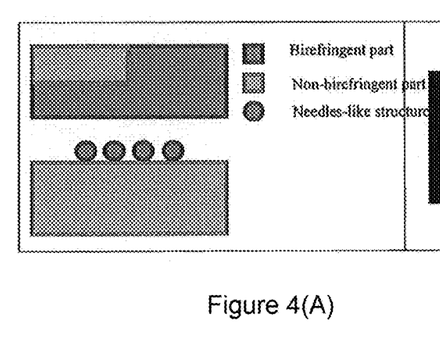
Figure 4B:
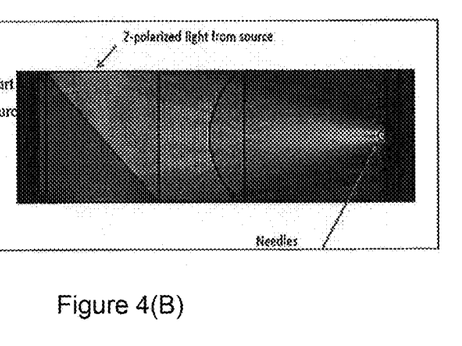

The paclitaxel birefringence response is studied with two geometries. One is a step profile and another includes paclitaxel needles as shown in FIG. 4. The step size and paclitaxel needles diameter geometries are summarized in table 2.

TABLE 2

Paclitaxel Optical Simulation Properties

| PTX step details | | PTX needle details | |
|---|---|---|---|
| Step size | 0.4 um | PTX needle dia. | 0.5 um |
| $n_o$ | 1.63 | Number of needles | 4 |
| $n_e$ | 1.64 | $n_o$ | 1.63 |

Figure 5A:
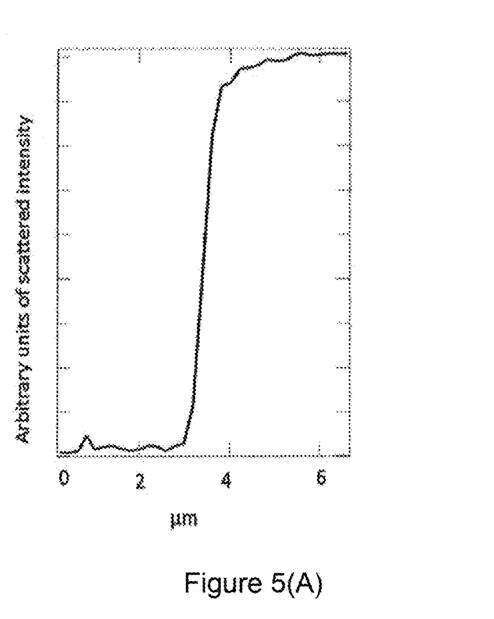
Figure 5B:
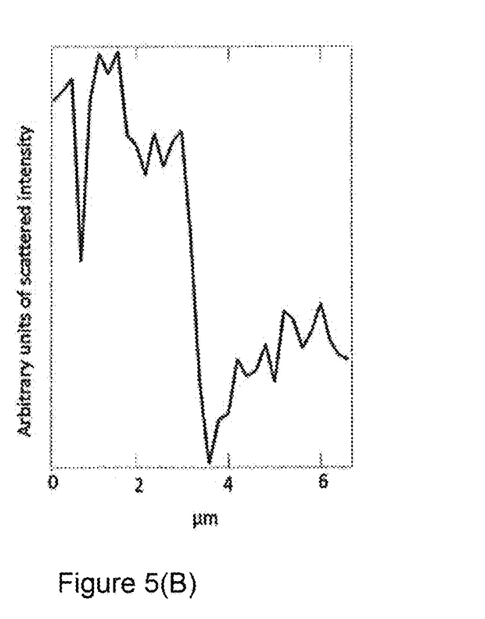

When the step profile is scanned with a focused laser beam at 380 nm wavelength using a 0.65 NA objective, the birefringent part of step rotates the polarization and high or low transmission occurs through the analyzer depending on nature of rotation. FIG. 5 shows the intensity response of a step profile at two different birefringence values of 0.01 and 0.001. According to the model, the polarization based microscope, produces very clean profile of intensity at birefringence of 0.01 and a noisy profile even at birefringence of 0.001. This indicates that the modelled microscope is responsive for even birefringence values of 0.001.

Birefringence of 0.001 is far lower than the actual birefringence of paclitaxel crystals. The sensitivity of microscope to the intensity depends on two factors: the extinction ratio of polarizer and the birefringence value of crystal. We have modelled the microscope with polarizer having extinction ratio of ~25. The higher extinction ratio, the more sensitive is the microscope. Due to modelling limitations, the polarizer extinction ratio is far smaller than optical polarizers used in experimental setups. We can expect sensitivity better than simulation in practical implementation.

We calculated the step size with intensity variation at the detector using equation 1 and compared this value with the model. The calculated values are expected to be within 5% of the actual values.

$$I = I^0 * (\cos^2((2\Pi/\lambda) * t * (n - \Delta n))) \quad 1$$

Where I is the intensity at detector, $I_o$ is the incident intensity on paclitaxel step, $\lambda$ is the wavelength of laser, t is the thickness of step, n is refractive index of paclitaxel and $\Delta n$ is the difference of refractive index of $n_o$ and $n_e$.

The simulation study was extended for paclitaxel needles of 0.5 dia. We have modelled four needles with birefringence of 0.01. Results are summarized in table 3.

TABLE 3

Calculated and modelled geometrical properties of paclitaxel

| Step profile thickness | | Needles thickness | |
|---|---|---|---|
| Actual steps size | 0.400 μm | Actual diameter | 0.500 μm |
| Calculated size | 0.418 μm | Calculated diameter | 0.476 μm |

Figure 6A:
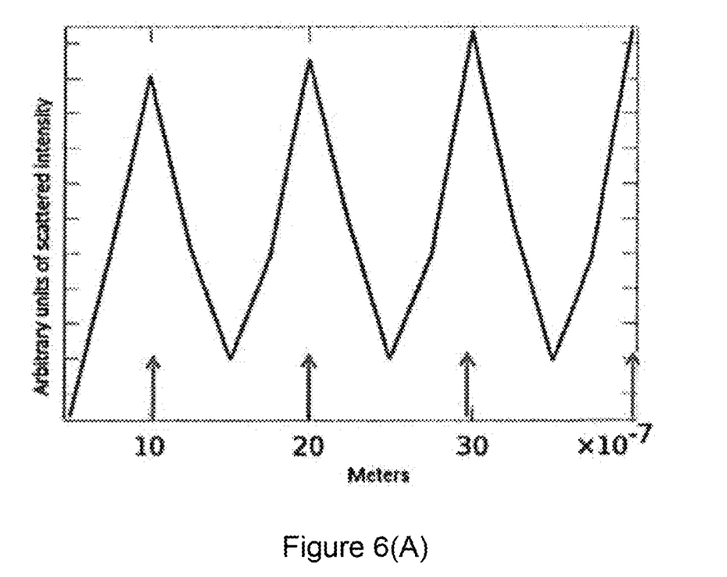
Figure 6B:
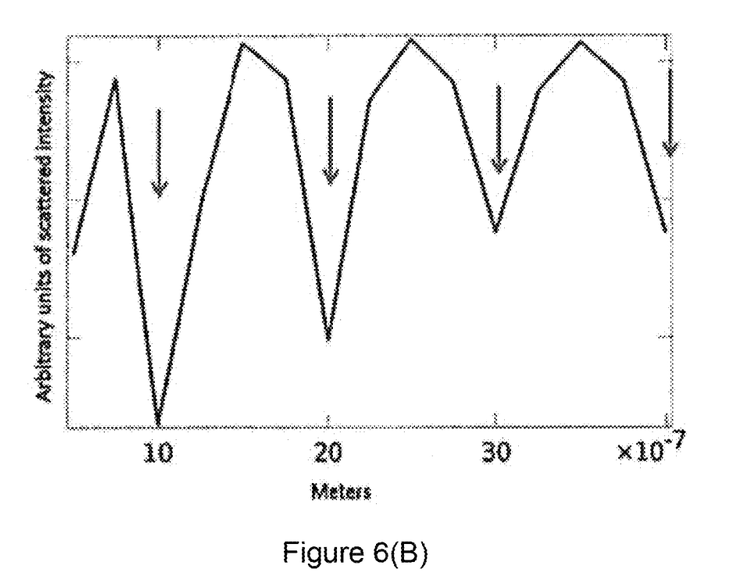
Figure 6C:
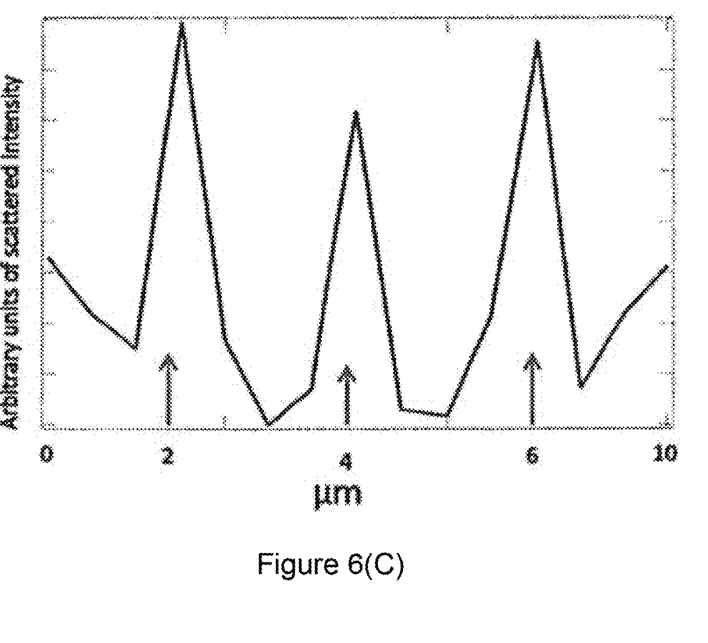
FIG. 6(C) is a graph showing modelled scattered intensity calculated at the detector of paclitaxel 3 needle-like structures using 229 nm.

FIG. 5 shows scattering intensity calculated at the detector with birefringence values set at 0.01 and 0.001. The arrows show the position of the needles. Scattered intensity from the needles at birefringence of 0.001 is corresponding to lower values unlike at birefringence of 0.01. This is because of the polarization rotation nature and incident polarization type. We also extended the simulation study for a 229 nm wavelength laser as the paclitaxel film absorbs radiation at this wavelength. This may allow for measuring the thickness of film without taking the polarization into the consideration. As a sharper focal spot is expected at lower wavelength, the peaks are sharper than that obtained at 380 nm wavelength as shown in FIG. 6(A-C). The sharper focal spot resulting from the diffraction limited spatial resolution scaling linearly with the inverse of the wavelength.

Example 3—Non-Birefringent Film Thickness Measurement

Figure 7A:
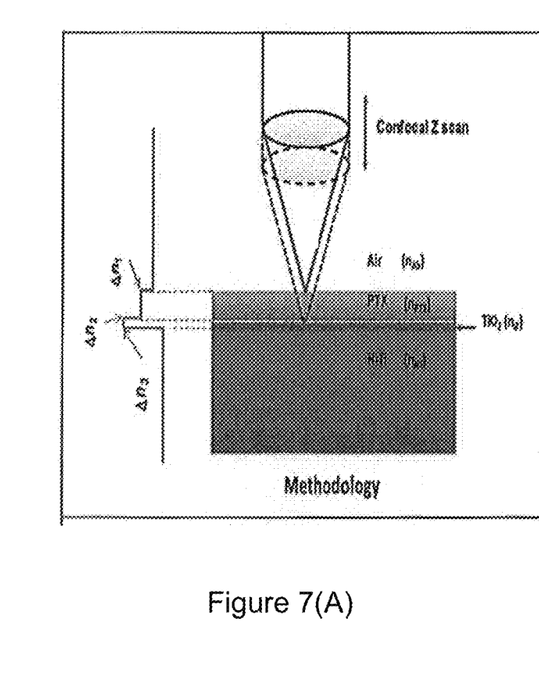
FIG. 7(A) is a schematic illustration showing a confocal used to determine film thickness.
Figure 7B:
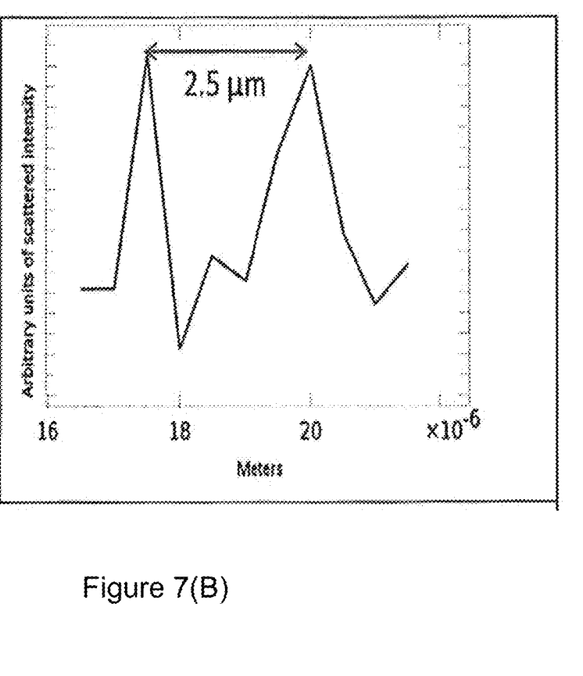
FIG. 7(B) is a graph showing modelled scattered intensity in axial scanning of the paclitaxel film.

If the paclitaxel film is birefringent, thickness can be calculated from the scattering intensity variation due to the polarization rotation of the reflected beam. If film is non-birefringent, thickness is determined by axial scanning confocal microscopy. When the laser beam or sample is scanned axially (in depth), higher scattering occurs due to the Fresnel reflection at two interfaces of paclitaxel film, one is paclitaxel-air interface and another is paclitaxel-NiTi (stent) interface. At these interfaces, a sudden variation of the refractive index is observed. In the model we measured the intensity variation caused by the jump in the refractive index. We observed two clear peaks at the two interfaces air/paclitaxel and paclitaxel NiTi. The thickness is calculated using the following formula:

$$t = n_{ptx} * \Delta z$$

Where t is the thickness of the paclitaxel and $\Delta z$ is the distance between the two peaks of scattered Intensities at interfaces.

We modelled the axial scanning microscope (Z-Scan) using COMSOL software and calculated the thickness of paclitaxel film, given that the theoretical thickness was 4 μm.

We observed two sharp peaks separated by 2.5 μm. According to the above formula, and using $n_{PTX}=1.63$, the corresponding calculated thickness is 4.075 μm. This is in a good agreement with the actual thickness. The method can measure the thickness with an error less than 2%.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A method for determining a distribution of a first polarization active compound in a coating, comprising:
    utilizing optical microscopy to obtain images at a plurality of planes at differing axial positions between an upper and a lower boundary of the coating;
    measuring a distribution of polarization activity within each of the images, wherein the distribution is based on a distribution in polarization of light within the plurality of images;

constructing a three dimensional distribution based on the distribution of polarization active material within each of the plurality of images; and determining the distribution of the first polarization active compound in the coating based on the three dimensional polarization activity distribution.

2. The method of claim 1, wherein the first polarization active compound is a crystalline taxane polymorph.

3. The method of claim 2, wherein the crystalline taxane polymorph is a crystalline paclitaxel polymorph.

4. The method of claim 3, therein coating is a coating on an implantable device.

5. The method of claim 4, therein the implantable device is selected from the group consisting of a stent and a balloon.

6. The method of claim 5, wherein the stent is a vascular stent.

7. The method of claim 1, wherein the coating consists essentially of the first polarization active compound and wherein the first polarization active compound is a drug.

8. The method of claim 7, wherein the drug of a taxane.

9. The method of claim 8, wherein the taxane is paclitaxel.

10. The method of claim 1, wherein the coating is free of a polymeric or non-polymeric carrier material.

11. The method of claim 1, further comprising determining a distribution of a second polarization active compound in the coating based on the three dimensional birefringence distribution, wherein the first polarization active compound and the second polarization active compound exhibit different polarization activity properties.

12. The method of claim 11, wherein the first polarization active compound and the second polarization active compound are crystalline polymorphs of paclitaxel.

13. The method of claim 12, wherein the first polarization active compound is dihydrate paclitaxel and wherein the second polarization active compound is anhydrous paclitaxel.

14. The method of claim 1, wherein the coating further comprises a non-polarization active drug.

15. The method of claim 1, wherein the optical microscopy is dual-beam confocal optical microscopy.

16. The method of claim 1, further comprising determining an axial position of a first and a second of the plurality of focal planes and determining a thickness of the coating based the axial position the first and the second focal planes; wherein the first focal plane is positioned at an upper boundary of the coating and wherein the second focal plane is positioned at a lower boundary of the coating.

17. The method of claim 1, there the optical microscopy comprises illuminating the coating with laser light at a wavelength selected from the group consisting of 786 nm, 380 nm and 229 nm.

18. A method for determining a distribution of a crystalline paclitaxel polymorph in a coating, comprising:

utilizing optical microscopy to obtain images at a plurality of focal planes at differing axial positions between an upper and a lower boundary of the coating;

measuring a polarization activity distribution within each of the plurality of images, wherein the polarization activity distribution is based on a distribution in polarization of light within the plurality of images;

constructing a three dimensional birefringence distribution based on the polarization activity distribution within each of the plurality of images; and determining the distribution of the crystalline paclitaxel polymorph in the coating based on the three dimensional polarization activity distribution, wherein the coating is a coating on an on an implantable vascular stent.

* * * * *